(12) United States Patent
Shi et al.

(10) Patent No.: US 8,131,377 B2
(45) Date of Patent: Mar. 6, 2012

(54) TELEMETRY LISTENING WINDOW MANAGEMENT FOR AN IMPLANTABLE MEDICAL DEVICE

(75) Inventors: Jess W. Shi, Winnetka, CA (US); Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1272 days.

(21) Appl. No.: 11/776,170

(22) Filed: Jul. 11, 2007

(65) Prior Publication Data
US 2009/0018618 A1    Jan. 15, 2009

(51) Int. Cl.
*A61N 1/08* (2006.01)
(52) U.S. Cl. .......................... 607/60; 128/903
(58) Field of Classification Search ............ 607/30–32, 607/59–62; 128/903–904
See application file for complete search history.

(56) References Cited

U.S. PATENT DOCUMENTS

| | | | |
|---|---|---|---|
| 5,088,488 A | 2/1992 | Markowitz et al. | 128/419 |
| 5,201,865 A | 4/1993 | Kuehn | 128/419 PT |
| 5,309,919 A | 5/1994 | Snell et al. | 128/697 |
| 5,314,458 A | 5/1994 | Najafi et al. | |
| 5,507,786 A | 4/1996 | Morgan et al. | 607/27 |
| 5,733,312 A | 3/1998 | Schloss et al. | 607/17 |
| 5,766,232 A | 6/1998 | Grevious et al. | 607/60 |
| 6,516,227 B1 | 2/2003 | Meadows et al. | 607/46 |
| 6,535,766 B1 | 3/2003 | Thompson et al. | 607/60 |
| 6,553,263 B1 | 4/2003 | Meadows et al. | 607/61 |
| 6,556,871 B2 | 4/2003 | Schmitt et al. | 607/60 |
| 6,868,288 B2 | 3/2005 | Thompson | 607/31 |
| 7,120,992 B2 | 10/2006 | He et al. | 29/606 |
| 7,177,698 B2 | 2/2007 | Klosterman et al. | 607/60 |
| 2002/0045920 A1 | 4/2002 | Thompson | 607/60 |
| 2003/0074036 A1 | 4/2003 | Prutchi et al. | 607/60 |
| 2003/0199939 A1 | 10/2003 | Schmitt et al. | 607/31 |
| 2004/0015205 A1 | 1/2004 | Whitehurst et al. | 607/48 |
| 2004/0059392 A1 | 3/2004 | Parramon et al. | 607/36 |
| 2005/0131495 A1 | 6/2005 | Parramon et al. | |
| 2005/0131496 A1 | 6/2005 | Parramon et al. | 607/61 |
| 2005/0277844 A1 | 12/2005 | Strother et al. | 600/546 |
| 2005/0277999 A1 | 12/2005 | Strother et al. | 607/48 |
| 2005/0278000 A1 | 12/2005 | Strother et al. | 607/48 |
| 2006/0276842 A1 | 12/2006 | He | 607/2 |

(Continued)

FOREIGN PATENT DOCUMENTS
WO    2005/123181 A2    12/2005
(Continued)

OTHER PUBLICATIONS
U.S. Appl. No. 11/550,655, filed Oct. 18, 2006, Parramon.
(Continued)

*Primary Examiner* — Carl H Layno
*Assistant Examiner* — Jessica Sarcione

(57) ABSTRACT

An improved arbitration scheme for allowing concurrent stimulation and telemetry listening in a microstimulator is disclosed. A listening window for telemetry is permitted to proceed, and access to the microstimulator's coil granted, during at least a portion of the inter-pulse period that follows the issuance of a stimulation pulse. This is permissible because access to the coil is not needed during the entirety of the inter-pulse period. For example, the listening window can issue during that portion of the inter-pulse period when the decoupling capacitor is discharged, but cannot issue during that portion of the inter-pulse period when the compliance voltage is being generated for the next stimulation pulse. However, because compliance voltage generation occupies only a small portion of the inter-pulse period, the technique is not substantially limited. By allowing the listening window to issue during the majority of the inter-pulse period, the listening window produces smaller gaps between the pulses, and stimulation therapy is thus brought closer to its ideal.

23 Claims, 5 Drawing Sheets

U.S. PATENT DOCUMENTS

| | | | |
|---|---|---|---|
| 2007/0060967 A1 | 3/2007 | Strother et al. | 607/31 |
| 2007/0060980 A1 | 3/2007 | Strother et al. | 607/61 |
| 2007/0088398 A1 | 4/2007 | Jacobson | 607/9 |
| 2007/0112403 A1 | 5/2007 | Moffitt et al. | 607/116 |
| 2007/0112404 A1 | 5/2007 | Mann et al. | 607/116 |
| 2007/0135865 A1 | 6/2007 | Schmitt et al. | 607/59 |
| 2007/0161919 A1 | 7/2007 | DiLorenzo | 600/544 |
| 2007/0167997 A1 | 7/2007 | Forsberg et al. | 607/61 |
| 2007/0270921 A1 | 11/2007 | Strother et al. | 607/60 |

FOREIGN PATENT DOCUMENTS

| | | |
|---|---|---|
| WO | 2005/123184 A2 | 12/2005 |
| WO | 2005/123185 A1 | 12/2005 |
| WO | 2007/047681 A2 | 4/2007 |
| WO | 2007/136657 A2 | 11/2007 |

OTHER PUBLICATIONS

Rodriguez et al.; "Flexible Communication and Control Protocol for Injectable Neuromuscular Interfaces;" IEEE Transactions on Biomedical Circuits and Systems; vol. 1 No. 1; Mar. 2007; pp. 19-27.

International Search Report and Written Opinion received in corresponding application No. PCT/US2008/068079 dated Oct. 2, 2008.

International Preliminary Report on Patentability regarding corresponding PCT application No. PCT/US2008/068079, dated Jan. 21, 2010.

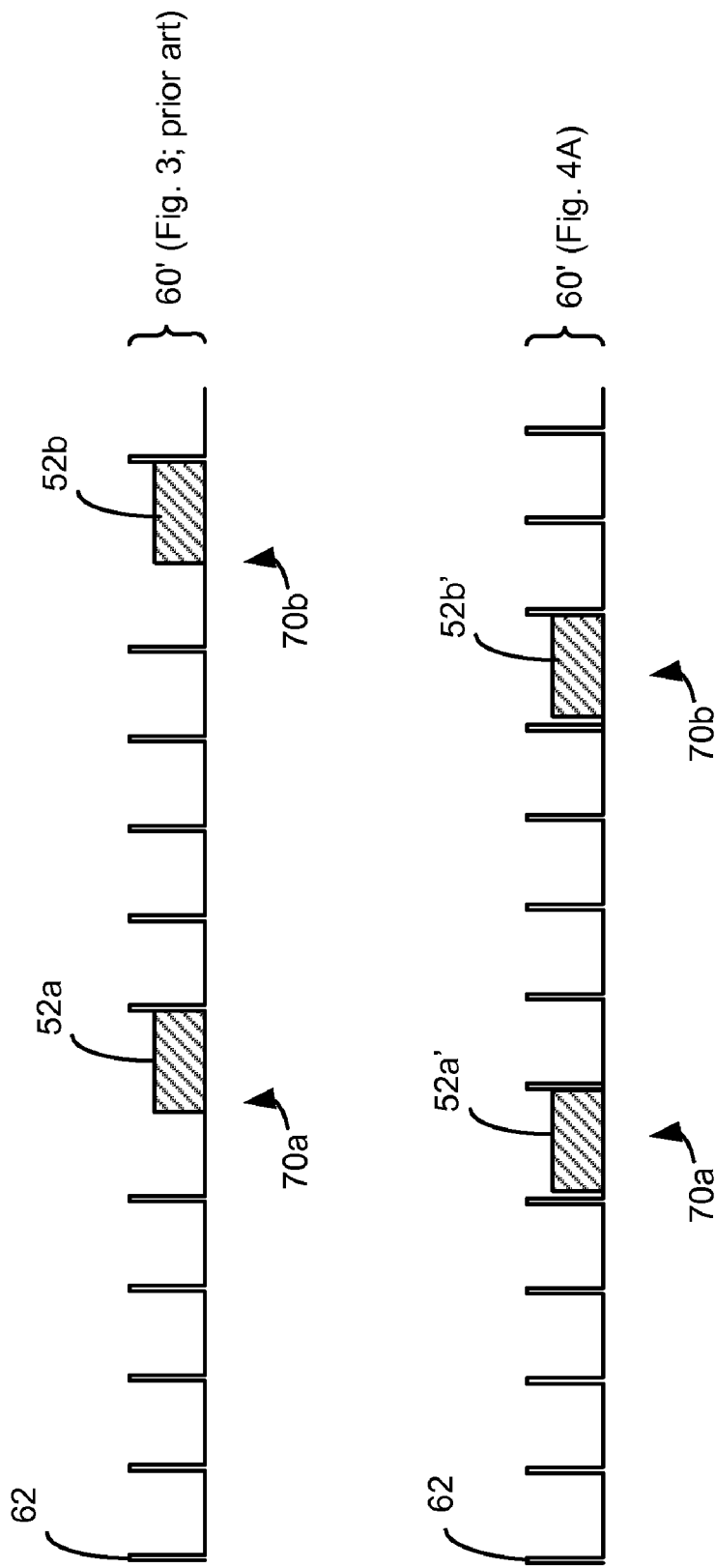

TELEMETRY LISTENING WINDOW MANAGEMENT FOR AN IMPLANTABLE MEDICAL DEVICE

FIELD OF THE INVENTION

The present invention relates generally to implantable stimulator devices, e.g., an implantable pulse generator such as a Bion® device, a Spinal Cord Stimulation (SCS) device, or other type of neural stimulation devices.

BACKGROUND

Implantable stimulation devices generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, occipital nerve stimulators to treat migraine headaches, and other neural stimulators to treat urinary incontinence, sleep apnea, shoulder sublaxation, etc. The present invention may find applicability in all such applications, although the description that follows will generally focus on the use of the invention within a microstimulator device of the type disclosed in U.S. Pat. Nos. 7,177,698; 7,120,992; 7,437,193; 7,702,385; 7,920,915; U.S. Patent Application Publications 2006/0276842, published Dec. 7, 2007, and 2004/0015205, published Jan. 22, 2004, all of which are incorporated herein by reference in their entireties. However, the present invention also has applicability in other implantable stimulator devices, such as Spinal Cord Stimulation (SCS) devices, examples of which can be found in U.S. Pat. Nos. 6,553,263 and 6,516,227, which are incorporated herein by reference in its entirety.

A microstimulator device typically comprises a small, generally-cylindrical housing which carries electrodes for producing a desired electric stimulation current. Devices of this type are implanted proximate to the target tissue to allow the stimulation current to stimulate the target tissue to provide therapy for a wide variety of conditions and disorders. A "microstimulator" in the context of this application means an implantable stimulator device in which the body or housing of the device is compact (typically on the order of a few millimeters in diameter by several millimeters to a few centimeters in length) and usually includes or carries stimulating electrodes intended to contact the patient's tissue. Generally, a microstimulator will include at least one anode electrode and at least one cathode electrode, either of which may comprise the housing of the microstimulator if it is conductive. Alternatively, microstimulators can have a plurality of either anodes or cathodes, such as is illustrated in U.S. Pat. No. 7,881,803, which is incorporated herein by reference in its entirety.

FIG. 1 illustrates exemplary circuitry within a microstimulator 10. The illustrated microstimulator comprises a single-anode/multi-cathode design, but could also comprise a single-anode/single-cathode or multi-anode/multi-cathode design. Therapeutic stimulation occurs as follows. The anode electrode 27 sources a current, I, into a resistance 24, R, i.e., the user's tissue. The return path for the current is provided by one or more cathodes 28, which can be selected via cathode switches 30. The magnitude of the current I is specified by a Digital-to-Analog Converter, or DAC 32, whose circuitry and structure is explained in the above-incorporated references. A decoupling capacitor 22, C, is disposed in the current path, usually proximate to the anode electrode 27. As is known, a decoupling capacitor 22 is useful in implantable stimulator devices to assist in charge recovery after the provision of a stimulation pulse, and to provide additional safety by preventing the direct injection of current to the patient's tissue 24.

The microstimulator 10 contains a battery 12 to power its various logic circuits, and to produce the energy necessary to provide the desired stimulation pulses at the electrodes 27, 28. When producing stimulation pulses, it is generally necessary to generate a compliance voltage, V+, from the battery voltage, Vbat. This is because it is generally necessary to tailor the voltage needed to produce the desired therapeutic current, I, and such tailoring is especially necessary when one considers that the resistance 24 of the patient's tissue will be variable.

Generation of the compliance voltage V+ from the battery voltage Vbat is the function of the compliance voltage generation circuitry 18. Compliance voltage generation circuitry 18 generally boosts the battery voltage to a higher compliance voltage V+, and thus comprises a DC-to-DC converter. (The circuitry 18 can also generate a compliance voltage lower than the battery voltage should that be warranted). The compliance voltage generation circuitry 18 uses a coil 15 within the microstimulator. As will be seen below, the coil 15 has other uses in the microstimulator 10. However, as concerns compliance voltage generation, the inductance of the coil 15 is used in conjunction with the V+ generation circuitry 18 (usually including at least one capacitor and at least one diode) to produce a desired compliance voltage, V+. Exemplary V+ generation circuitry employing a coiled inductor to produce the compliance voltage in an implantable medical device is disclosed in U.S. Pat. No. 7,379,775, which is incorporated herein by reference in its entirety.

As just noted, the coil 15 can be used for other purposes within the microstimulator 10. As shown in FIG. 2, the coil 15 can also be used as a means for wirelessly receiving power from an external charger 40, and for wirelessly receiving data from an external programmer 45. These external devices are typically separate from each other, but could be integrated as well. As is well known, the external charger 40 is typically a hand-held device used to recharge the battery 12 within the microstimulator. (In other embodiments, the external charger 40 can also be used to continuously provide energy to an implant otherwise lacking a battery). The external programmer 45 is also typically hand held, and is used by a clinician or patient to send data to the microstimulator 10. For example, by manipulating a user interface (not shown) on the external programmer 45, a clinician can provide a therapy program tailored for a particular patient, which program might specify the amplitude, pulse width, and frequency of the stimulation pulses to be provided to the patient.

These external devices also contain coils 41, 46, which are energized to create magnetic fields, which in turn induce currents in the coil 15 within the microstimulator 10. During charging, energy induced in coil 15 from coil 41 is rectified and passed via charging and battery protection circuitry 14 (FIG. 1) to the battery 12, which allows the battery 12 to be safely charged to a value of about 4.1V for example. During data telemetry, coil 46 in the external programmer 45 is likewise energized, typically using a Frequency Shift Keying (FSK) modulation protocol. Again, the resulting magnetic field induces a current in the coil 15, and the resulting received signal is demodulated at telemetry circuitry 16 to recover the transmitted data. Data telemetry can also occur in the other direction, i.e., from the coil 15 to the coil 46 to allow the microstimulator 10 to report to the external programmer 45 concerning its status, and in this regard the telemetry circuit 16 can comprise both transmitter and receiver circuitry.

From the foregoing, it should be appreciated that the coil 15 in the microstimulator 10 is implicated in compliance voltage generation, battery recharging, and telemetry. The use of one coil 15 to perform different functions in a microstimulator 10 is advantageous: space is limited within the housing of the microstimulator, which tends to limits the number of discrete coils that can be used. Accordingly, it is generally necessary for the microcontroller 20 in the microstimulator 10 to arbitrate or time-multiplex the use of the coil 15 so that the various functions will not be in conflict. For example, during charging, telemetry circuitry 16 and V+ generation circuitry 18 are typically disabled by the microcontroller 20, ensuring that the coil 15 will only be used to assist in recharging the microstimulator's battery 12.

However, compliance voltage generation and data telemetry can generally run concurrently, and it is therefore necessary for the microcontroller 20 to decide which of these two functions can have access to the coil 15 at a given time. To better understand this, it is useful to review how data telemetry operates in the system. Should the external programmer 45 need to communicate with the microstimulator 10, the external programmer 45 will continually broadcast a handshaking message, and wait for an acknowledgment from the microstimulator 10 that it is ready to receive data. The microstimulator 10, in turn, must periodically "listen" for this handshaking message. Such listening occurs only periodically, and only during a listening window 52 of limited duration, $D(t)$, as illustrated in FIG. 3. The telemetry circuitry 16 is enabled, and the coil 15 reserved for telemetry, during the listening window 52. The duration of the listening window 52 may be about 20 milliseconds (ms) or so, and ideally occurs periodically, $T(t)$, every 100 ms or so. However, such periodicity is variable as explained below.

Compliance voltage generation occurs during the provision of therapeutic stimulation to a patient. An exemplary therapy of stimulation 60 is shown in FIG. 3. Essentially, the stimulation 60 can be understood as an alternating sequence of pulses 62 and inter-pulse periods 64. The pulses 62 correspond to points in time in which the desired therapeutic current, I, is provided to patient. Such pulses 62 typically will not exceed a duration $D(p)$ of 1 ms, and may be as low as 10 microseconds in duration.

Two primary events occur during the inter-pulse period 64 after each pulse 62. First, the compliance voltage for the next pulse is generated; this is generally necessary because the issuance of the pulse will have loaded the compliance voltage to below a level suitable for the next pulse. As mentioned earlier, generation of the compliance voltage requires activation of the V+ generation circuitry 18, and access to the coil 15. Second, the decoupling capacitor 22 (C) is discharged during the inter-pulse period 64. As disclosed in the above-incorporated U.S. Pat. No. 7,881,803, this typically occurs by coupling both the anode and the selected cathode(s) to the battery voltage, Vbat, which has the effect of shorting both sides of the decoupling capacitor 22 through the patient's tissue 24. Generally, the duration, $D(r)$, of the inter-pulse period 64 is variable, and depends on the frequency, $f(s)$, of the stimulation pulses chosen as effective for the patient. The inter-pulse period duration generally cannot be less than a certain minimum, which guarantees sufficient time to perform the necessary inter-pulse tasks of compliance voltage generation and output capacitor discharge. The reality of a minimum duration for the inter-pulse period in turns limits the maximum frequency $f(s)$ that can be chosen for the stimulation timing signal 60, but such limit is normally beyond that required for useful therapy and hence does not substantially limit the utility of the microstimulator 10.

As noted earlier, the need to concurrently issue stimulation and to listen for telemetry requires the microcontroller 20 to arbitrate access to the coil 15. How this occurred in the prior art is illustrated in FIG. 3. Illustrated are exemplary ideal timing signals for both telemetry listening (50) and for stimulation (60). As regards telemetry listening, it is seen that the listening windows 52 are ideally set to a duration $D(t)$ of 20 ms, and occur with a periodicity $T(t)$ of 100 ms. The stimulation timing signal 60 in the example has been chosen with a pulse duration $D(p)$ of 1 ms, and a frequency $f(s)$ of 55.555 Hz. Working the math, this equates to an inter-pulse period duration $D(r)$ of 17 ms, for a total stimulation period $T(s)$ of 18 ms.

Assuming these exemplary values, arbitration logic 21 within the microcontroller 20 will cause both the telemetry listening timing signal (50) and the stimulation timing signal (60) to deviate from ideal values. This is because the arbitration logic 21 treats each stimulation cycle 65 (comprising a pulse 62 and an inter-pulse period 64) and each listening window 52 as blocks that cannot overlap in time. Therefore, the microcontroller 20, when arbitrating, will not grant priority to a listening window 52 until the currently-pending stimulation cycle 65 has completed. For example, in FIG. 3, the ideal timing of listening window 52a overlaps with the finishing of stimulation cycle 65a. Therefore, and as shown in the non-ideal telemetry timing signal 50' resulting from the arbitration, listening window 52a' is made to wait until the close of stimulation cycle 65a, i.e., until the inter-pulse period 64 within that cycle has completed. Once the listening window 52a' has issued, it will need unencumbered access to the coil 15. Therefore, the next stimulation cycle 65b' cannot start until the end of the listening window 52a', as shown in non-ideal stimulation timing signal 60'.

Because of the arbitration scheme used to mitigate conflicts regarding coil 15 access, a non-ideal telemetry listening timing signal 50' and a non-ideal stimulation timing signal 60' result. The non-ideal telemetry listening timing signal 50' results in a slightly longer period (e.g., $T(t)$=110 ms) between listening windows 52' when compared to what was otherwise desired as ideal (100 ms). However, such a minor increase in this period $T(t)$ is not significant or problematic.

By contrast, the resulting non-ideal stimulation timing signal 60' is potentially problematic. As can be seen in FIG. 3, the result of the arbitration scheme results in prolonged gaps 70a, 70b, etc. in the stimulation pulses 62. These gaps 70a are significantly longer (37 ms) than what was otherwise deemed as ideal therapy for the patient (17 ms), and occur with significant frequency (e.g., every sixth pulse in the example of FIG. 3). Such gross deviations from the ideal may be perceptible by the patient, and hence are greatly disfavored.

Accordingly, the implantable stimulator art, and particularly the microstimulator art, would benefit from an improved technique to allow concurrent stimulation and telemetry listening that does not cause large deviations of the stimulation pulses from their ideal timings.

BRIEF DESCRIPTION OF THE DRAWINGS

FIGS. 4A and 4B illustrate the disclosed improved arbitration scheme, and illustrates how the improve scheme causes a smaller deviation of the stimulation pulses from their ideal timings when compared with the prior art technique of FIG. 3.

DETAILED DESCRIPTION

Figure 1:
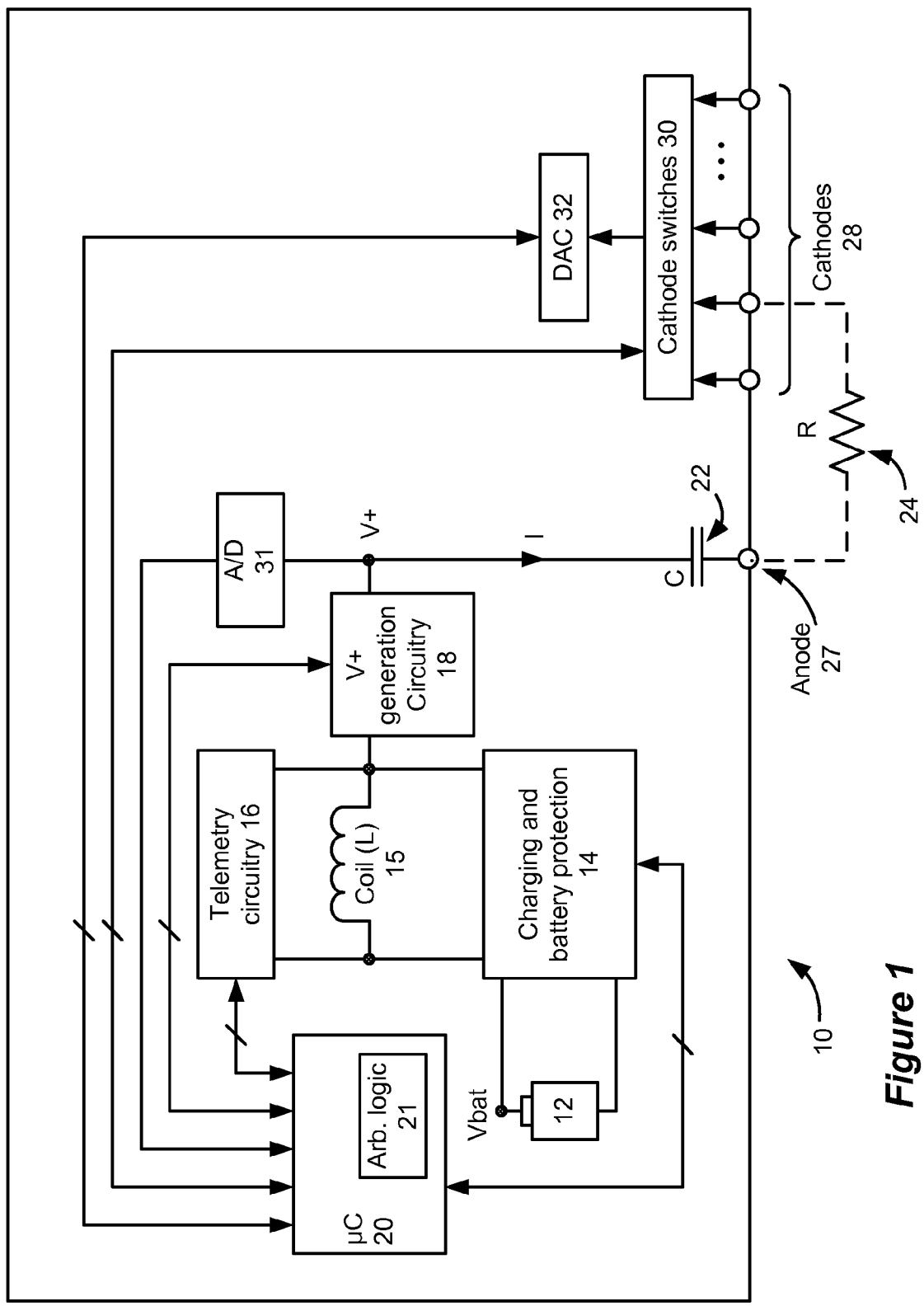
FIG. 1 illustrates circuitry within an implantable microstimulator, and specifically shows various functional blocks (telemetry, charging, boosting) needing access to the microstimulator's singular coil.
Figure 2:
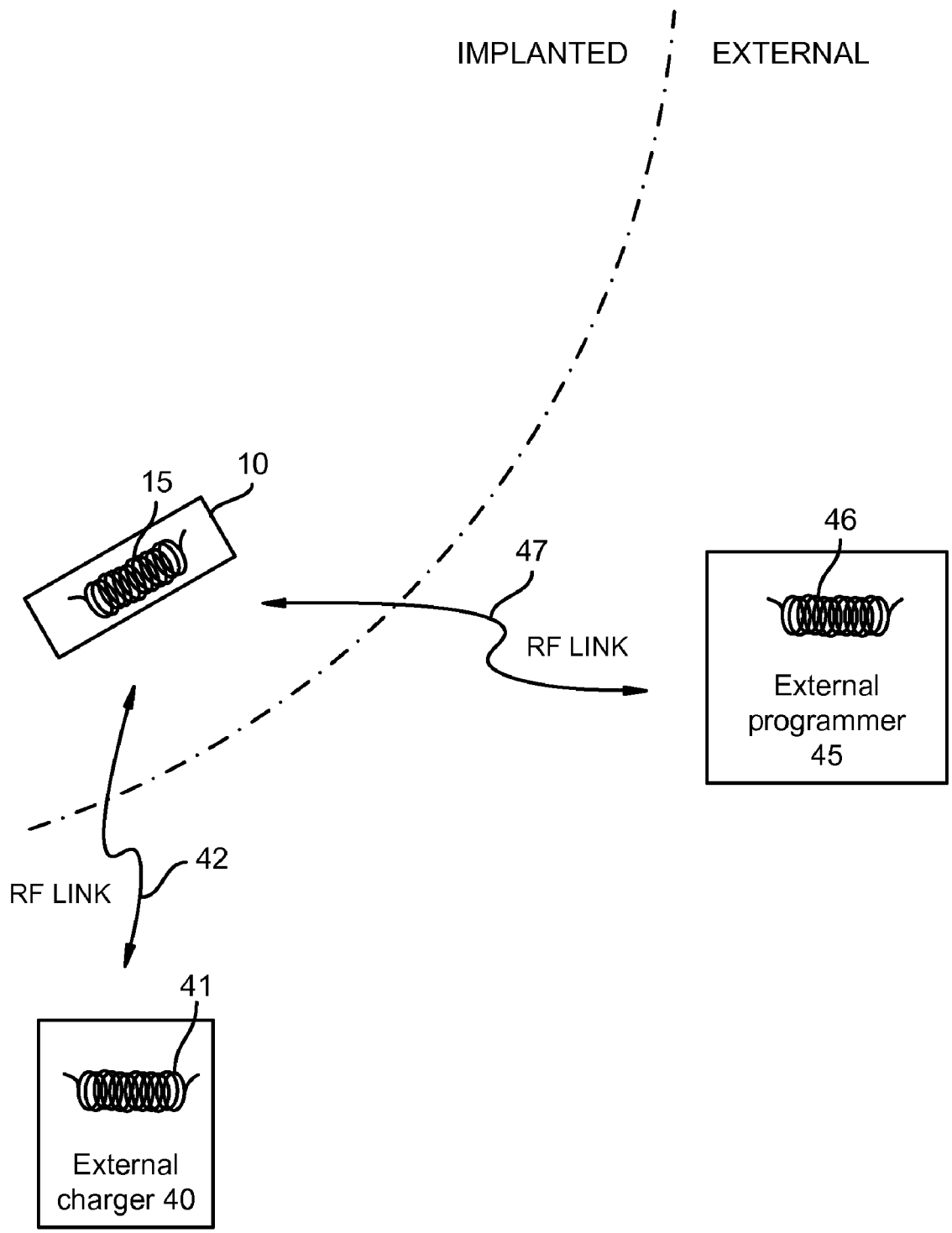
FIG. 2 shows the microstimulator of FIG. 1 as implanted in a patient, and further shows an external charger and an external programmer in wireless communication with the microstimulator using their respective coils.

An improved arbitration scheme for allowing concurrent stimulation and telemetry listening in a microstimulator or other implantable pulse generator is disclosed. A listening window for telemetry is permitted to proceed, and access to the microstimulator's coil granted, during at least a portion of the inter-pulse period that follows the issuance of a stimulation pulse. This is permissible because access to the coil is not needed during the entirety of the inter-pulse period. For example, the listening window can issue during that portion of the inter-pulse period when the decoupling capacitor is discharged, because discharging of the decoupling capacitor des not require access to the coil. By contrast, the listening window cannot issue during that portion of the inter-pulse period when the compliance voltage is being generated for the next stimulation pulse, because compliance voltage generation does require access to the coil. However, because compliance voltage generation occurs relatively quickly and occupies only a small portion of the inter-pulse period, not being able to issue the listening window during that inter-pulse period portion does not significantly limit the technique. By allowing the listening window to issue during the majority of the inter-pulse period, the listening window produces smaller gaps between the pulses. As a result, the stimulation pulses are issued at closer to their ideal positions, and the patient is less likely to perceive a difference from otherwise ideal therapy arising from the telemetry listening window.

Central to the disclosed technique is the recognition that the access to the coil 15 within the microstimulator 10 is not required during the entirety of the inter-pulse period 64. As noted earlier, two primary events happen during the inter-pulse period 64: compliance voltage generation to form a suitable voltage to power the next stimulation pulse 62; and discharging of the decoupling capacitor 22 (C). The timing of these two inter-pulse functions is illustrated in FIG. 4A, which once again shows an ideal stimulation timing signal 60 for a given patient. As illustrated, both compliance voltage generation and decoupling capacitor discharge occur in parallel during the inter-pulse period 64, and both of these functions begin essentially immediately after the issuance of a preceding stimulation pulse 62. (In reality, other functions will occur in the microstimulator 10 between the end of a stimulation pulse 62 and the recover period 64 functions, but these are immaterial and/or negligible when compared to the time scales being discussed).

It has been observed by the inventors that compliance voltage generation occurs relatively quickly during the inter-pulse period 64, whereas discharging of the decoupling capacitor 22 occurs relatively slowly. The duration of compliance voltage generation, D(g), typically occurs in under a millisecond. By contrast, the duration necessary to discharge the decoupling capacitor, D(c), can take up to ten milliseconds or more. Ultimately, the decoupling capacitor discharge duration D(c) will be proportional to the product of the width and amplitude of the stimulation pulse, and thus will be variable, but regardless is typically at least five to ten times longer than the duration D(g) necessary for compliance voltage generation.

The difference in these durations D(g) and D(c) is significant to the problem of interruption of the stimulation pulses 62 by the listening window 52, especially when one considers the impact on the coil 15. Decoupling capacitor discharge does not require coil 15 access. Therefore, the telemetry listening window 52 (where telemetry listening does require access to the coil) can be arbitrated to occur concurrently with decoupling capacitor discharge. However, because compliance voltage generation does require access to the coil, the telemetry listening window 52 cannot be arbitrated to occur concurrently with compliance voltage generation.

Figure 4A:
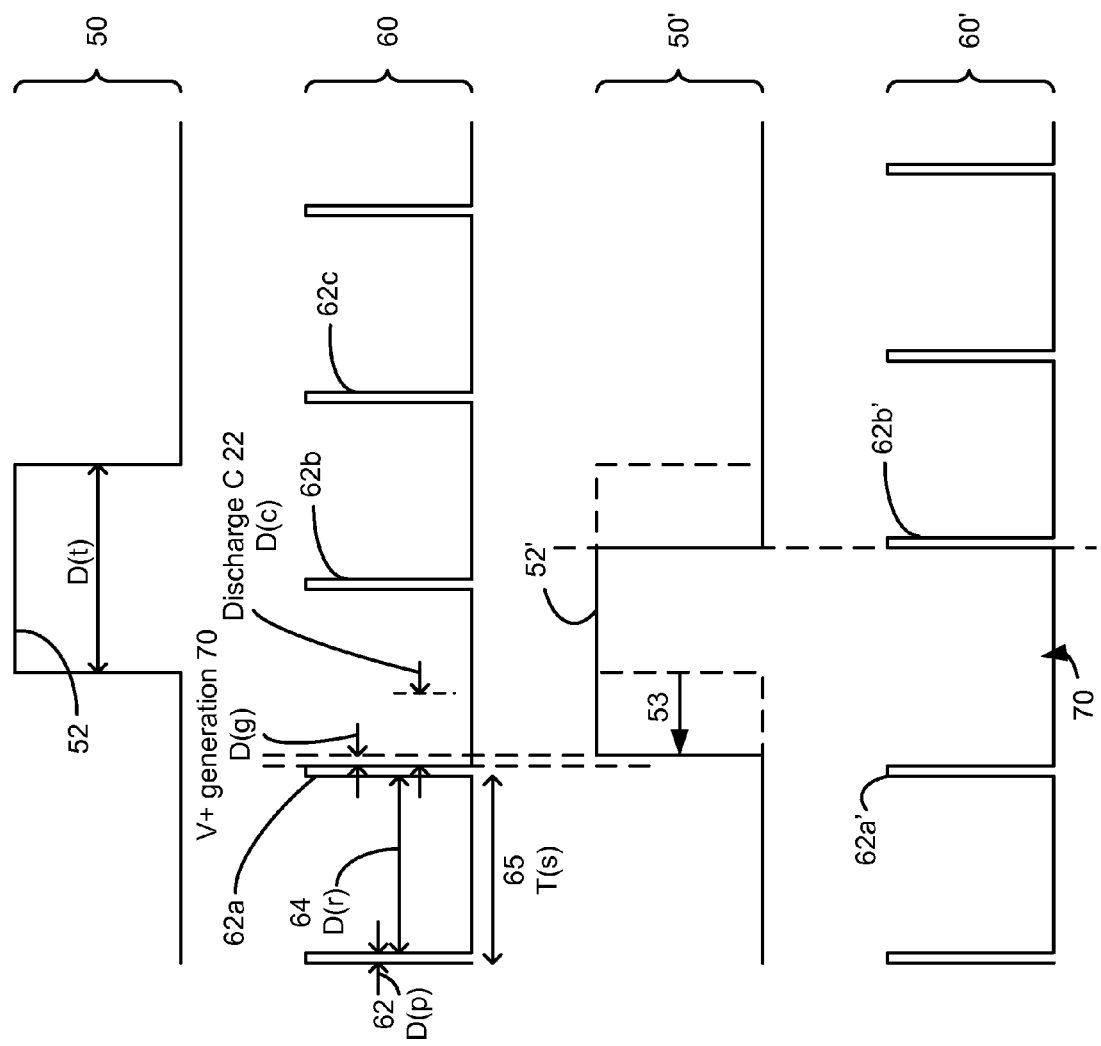

The effect, according to an embodiment of the disclosed technique, is that the microcontroller 20 can allow the listening window 52 to issue after compliance voltage generation has finished (i.e., after duration D(g)), but concurrently with discharging of the decoupling capacitor. This is shown in the improved telemetry listening timing signal 50' of FIG. 4A. As shown, the listening window 52' has been moved 53 from its ideal position (50) and into a portion of the inter-pulse period 64 such that it is issued after compliance voltage generation, D(g). Then, as before, the next stimulation pulse 62b' can issue after the listening window has completed. While FIG. 4A illustrates moving the listening window 52' to an earlier time, arbitration in accordance with the disclosed technique could also move the listening window 52' later in time, such that it occurs after compliance voltage generation of the next pulse 62b, i.e., between pulses 62b and 62c. Ultimately, it is not important to the technique whether the listening window 52' is moved earlier or later in time from its ideal position (50), because, either way, the periodicity of the listening window T(t) is changed by an insignificant amount.

Figure 3:
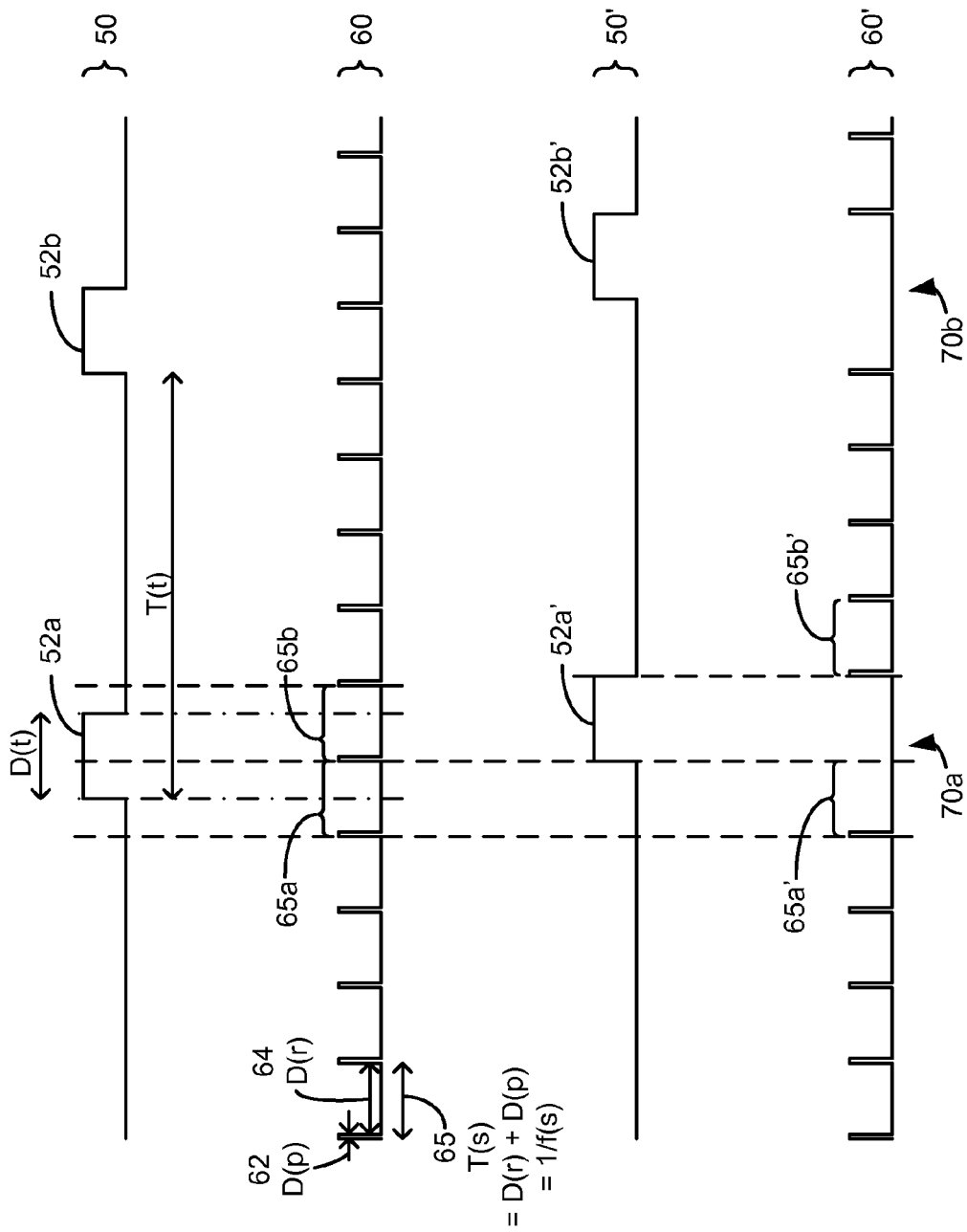
FIG. 3 illustrates ideal timing signals representing stimulation and telemetry listing, and further illustrates how those waveforms deviate from the ideal in the prior art because of arbitration schemes design to prevent concurrent use of the singular coil.

By allowing the listening window 52 to encroach upon "non-coil-utility" portions of the inter-pulse period 64, it is seen that the listening window gap 70 between stimulation pulses 62 is greatly reduced when compared with the prior art technique illustrated in FIG. 3. This comparison is best shown in FIG. 4B, which shows the resulting non-ideal stimulation timing signals 60' using the prior art technique (FIG. 3) and the disclosed technique (FIG. 4A), with listening windows 52 or 52' interspersed to understand their relations to the stimulation pulses 62. To continue the example discussed herein, when compared to an ideal inter-pulse period D(r) of 17 ms, the disclosed technique produces a gap 70 of 21 ms (D(g)+D(t)), compared to a gap 70 of 37 ms (D(r)+D(t)). The resulting stimulation timing signal 60' is thus much closer to the ideal 60 using the disclosed technique, and accordingly is less likely to be perceived by the patient.

Moreover, if the listening window 52 has a relatively short duration D(t) compared to the duration D(r) of the inter-pulse period 64 in a given application, use of the disclosed technique can eliminate an excessive gap 70 altogether, with the result that the resulting stimulation timing signal 60' is perfectly ideal. This would occur when the sum of the duration of compliance voltage generation D(g) plus the duration of the listening window D(t) is less or equal to than the duration of the needed inter-pulse period D(r) (i.e., when $D(g)+D(t) \leqq D(r)$).

Implementing the disclosed technique is relatively simple and requires only software modifications (not hardware modification) to an otherwise standard microstimulator 10, and specifically requires software modifications to the arbitration logic 21. Thus, and referring again to FIG. 1, notice that the magnitude of the compliance voltage V+ produced by the V+ generation circuitry 18 is monitored by the microcontroller 20 via an A/D converter 31 (which may be integrated with the microcontroller). Because this feedback path is typically already present for other reasons (e.g., to monitor and protect against excessive, unsafe compliance voltage generation), it can exploited by appropriate software modification to the arbitration logic 21 to be used during listening window arbitration. Specifically, the arbitration logic 21 can assess whether the microstimulator 10 is currently within an inter-pulse period 64, and if so, whether the compliance voltage V+ has been generated to a suitable level, e.g., whether D(g) has passed, or whether a certain magnitude for V+ has been reached. If so, the arbitration logic 21 can allow the listening window 52 to issue by enabling the telemetry circuitry 16 as appropriate in accordance with the technique disclosed herein.

Although disclosed in the context of improving the timing for the issuance of a telemetry listening window, it should be understood that the disclosed technique is not so limited. For example, the disclosed technique can be used to improve the timing of any sort of periodically-issued telemetry window, even if that window's purpose is not to listen for telemetry from an external device. For example, time-arbitrated telemetry windows can be used to periodically receive data from or transmit data to the external device, even while stimulation is occurring. Thus, using the disclosed technique, programming data could be gradually received over a number of telemetry windows while stimulation pulses are being provided to the patient. Or, the microstimulator could use the telemetry windows to periodically provide information concerning its status to the external device, again while stimulation pulses are being provided to the patient.

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. A method implementable in an implantable stimulation device for enabling telemetry concurrent with provision of stimulation pulses to a patient, comprising:
    issuing a series of successive stimulation cycles, wherein the stimulation cycles comprise a stimulation pulse and an inter-pulse period; and
    issuing a plurality of telemetry windows by periodically issuing after at least one stimulation cycle a telemetry window during which the implantable stimulation device can communicate with an external device;
    wherein the telemetry windows are interposed between successive stimulation cycles, and wherein the telemetry windows encroach upon at least a portion of an inter-pulse period of one of the successive stimulation cycles.

2. The method of claim 1, wherein the telemetry windows comprise listening windows for listening for a handshaking message from the external device.

3. The method of claim 1, wherein the at least a portion of the inter-pulse period upon which the telemetry windows encroach comprises a portion during which a current path decoupling capacitor is discharged.

4. The method of claim 1, wherein the implantable stimulation device comprises a microstimulator with a single coil.

5. The method of claim 4, wherein the at least a portion of the inter-pulse period upon which the telemetry windows encroach does not comprise a portion during which compliance voltage generation circuitry has access to the coil.

6. The method of claim 1, wherein the stimulation pulses are issued to at least one electrode on the implantable stimulation device.

7. The method of claim 1, wherein each telemetry window issues after a plurality of stimulation cycles.

8. A method implementable in an implantable stimulation device for enabling telemetry concurrent with provision of stimulation pulses to a patient, the implantable stimulation device comprising a coil, at least one electrode for providing stimulation pulses to the patient's tissue, telemetry circuitry for communicating with an external device, compliance voltage generation circuitry for producing a voltage at the at least one electrode, and at least one decoupling capacitor in a current path of the at least one electrode, the method comprising:
    issuing a sequence of stimulation pulses to the at least one electrode with intervening inter-pulse periods, wherein the inter-pulse periods comprise a first portion during which the coil is accessed by the compliance voltage generation circuitry and a second portion during which the decoupling capacitor is discharged; and
    issuing a plurality of telemetry windows by periodically issuing after at least one stimulation pulse a telemetry window during which the implantable stimulation device can communicate with an external device, wherein the coil is accessed by telemetry circuitry during the telemetry windows;
    wherein the telemetry windows are interposed between successive stimulation pulses during at least a part of the second portions of the inter-pulse periods between the successive stimulation pulses, but not during the first portions of the inter-pulse periods between the successive stimulation pulses.

9. The method of claim 8, wherein the telemetry windows comprise listening windows for listening for a handshaking message from the external device.

10. The method of claim 8, wherein the coil comprises the only coil within the implantable stimulation device.

11. The method of claim 8, wherein the first and second portions overlap.

12. The method of claim 8, wherein the at least one electrode is included on or is carried by housing of the implantable stimulation device.

13. The method of claim 8, wherein the decoupling capacitor is discharged by coupling each side of the capacitor to a battery voltage through the patient's tissue.

14. The method of claim 13, wherein the compliance voltage generation circuitry generates a first voltage at the at least one electrode from the battery voltage.

15. The method of claim 8, wherein each telemetry window issues after a plurality of stimulation pulses.

16. An implantable stimulation device, comprising:
    a coil;
    at least one electrode for providing stimulation pulses to a patient's tissue;
    telemetry circuitry for communicating with an external device;
    compliance voltage generation circuitry for producing from a battery voltage a first voltage at the at least one electrode; and
    arbitration logic, wherein the arbitration logic grants the telemetry circuitry access to the coil to enable communication with an external device during at least a portion of a stimulation cycle comprising a stimulation pulse and an inter-pulse period, wherein the arbitration logic enables the telemetry circuitry during at least the portion of the inter-pulse period of the stimulation cycle, but not during a portion of the inter-pulse period of the stimulation cycle when the compliance voltage generation circuitry has access to the coil.

17. The device of claim 16, wherein the telemetry circuitry is granted access to the coil for the purpose of listening for a handshaking message from the external device.

18. The device of claim 16, wherein the device comprises a microstimulator.

19. The method of claim 16, wherein the at least one electrode is included on or is carried by housing of the implantable stimulation device.

20. The device of claim 16, wherein the arbitration logic comprises a portion of a microcontroller within the implantable stimulation device.

21. The device of claim 16, further comprising at least one decoupling capacitor in a current path of the at least one electrode, and wherein the arbitration logic enables the telemetry circuitry during at least the portion of the inter-pulse period when the decoupling capacitor is being discharged.

22. The device of claim 2, wherein the decoupling capacitor is discharged by coupling each side of the capacitor to the battery voltage through the patient's tissue.

23. The implantable stimulation device of claim 16, wherein the coil comprises a singular coil.

* * * * *